United States Patent [19]

Harris

[11] Patent Number: 5,030,202
[45] Date of Patent: Jul. 9, 1991

[54] LAVAGE SYSTEM
[75] Inventor: Leverne J. C. Harris, Rockwood, Canada
[73] Assignee: EquiBov Ltd., Rockwood, Canada
[21] Appl. No.: 350,956
[22] Filed: May 12, 1989
[51] Int. Cl.$^5$ .............................................. A61M 1/00
[52] U.S. Cl. ..................................... 604/27; 604/39; 604/41
[58] Field of Search ..................... 604/27, 43, 54, 55, 604/39.41, 35, 19, 73

[56] References Cited
U.S. PATENT DOCUMENTS

3,144,868  8/1964  Jascalevich ........................... 604/43
3,527,203  9/1970  Gravlee ................................. 604/41
4,861,338  8/1989  Meador ................................. 604/39

Primary Examiner—Stephen C. Pellergrino
Assistant Examiner—Michael Rafa
Attorney, Agent, or Firm—Rogers, Bereskin & Parr

[57] ABSTRACT

Lavage apparatus comprises lavage fluid supply apparatus, a first catheter having a distal end for positioning in the uterus of an animal and a proximal end for communication with the lavage fluid supply, a pair of bilateral catheters connected to the proximal end of the first catheter for extending into respective horns of the uterus, and catheter locating means for locating the catheters in the uterus. The first catheter defines respective supply and drain lumens. The bilateral catheters each define respective lumens for fluid communication between the supply lumen and the interior of the respective uterine horn. The lavage fluid supply apparatus may include a pump for supplying lavage fluid under pressure. The supply may also include a lavage fluid storage tank for containing a volume of fluid, and a heater to maintain the temperature of the stored fluid within a predetermined range. For use in a gravid uterus, a drain tube may be provided at the distal end of the first catheter for reaching into the depths of the uterus. Further, vacuum drainage apparatus may be provided to drain lavage fluid from the uterus. If desired, the lavage fluid supply may be utilized for purposes other than uterine lavages such as, for example, supplying fluids for intravenous infusion.

70 Claims, 10 Drawing Sheets

LAVAGE SYSTEM

FIELD OF THE INVENTION

This invention relates to a lavage system, and to the various components of the system. The system has particular application in uterine lavages for mares.

BACKGROUND OF THE INVENTION

Uterine Lavage

Post partum mares usually come into heat around nine days after foaling. However, the conception rate of mares bred at this time is low, typically in the 35-55% range. The conception rates of mares coming into heat for the second or third times, approximately eighteen or twenty seven days after foaling, respectively, is generally higher, though this requires the mare to be bred again, at added expense, and also leads to a loss in the mare's productivity. This low initial conception rate may be related to a number of factors, including retained placenta or metritis (infection) in the uterus, as well as poor involution post foaling, excessive lochia and low grade endometritis as a result of both physiological and confinement management practises.

In an effort to decrease levels of infection, practitioners have often treated mares with antibiotics following foaling. However, this is expensive, and the wide spread use of antibiotics in such circumstances is discouraged as it tends to increase levels of antibiotic resistance. This approach also ignores subinvolution, one of the main problems encountered with post partum mares.

Flushing of the uterus with sterile fluid, possibly containing antibiotics, has also been used to clear the uterus of retained placenta and reduce levels of infection. The flushing is achieved by use of gravity to feed lavage fluid from a funnel through a flexible tube into the uterus. The fluid drains by siphon effect through a second tube leading from the uterus, or through the same tube, after the lavage fluid has been passed into the uterus. This method is fairly well known among practitioners, but requires the presence of two people, one to locate the tubes and the other to dispense the fluids, and is also time consuming and awkward. It is also difficult to control the rate of flow of lavage fluid into the uterus, and it is not possible to sterilize the apparatus. Further, it is desirable to use hot water to carry out the lavage, and this requires water to be heated and then transported to the lavage site. Understandably, in these circumstances, control of the temperature of the water is difficult. Understandably, the amount of work and organization required to carry out such a flushing operation precludes its use except in the most severe or valuable of cases.

Uterine flushing is also utilized in the collection of embryos (fertilized ova) from animals, as in for example Canadian Patent No. 1,073,286, issued on Mar. 11, 1980, to the Milk Marketing Board, which discloses "Apparatus For Use In Collecting Eggs from Animals". The apparatus includes a flexible, small diameter catheter for insertion into the vagina of an animal and through the cervix, the insertion assisted by use of an outer plastic sheath and a rigid tubular member. The catheter is located in the cervix with an inflatable cuff anterior to the cervix and defines a plurality of lumens, one an air passage for the inflatable collar, one for supplying fluid, and the remaining one acting as a drain. In use, the end of the catheter, and also the end of the supply lumen, is located well into one of the uterine horns. Fluid is supplied using a syringe, typically of 60 ml capacity, operated by an assistant, through the supply lumen into the uterine horn and withdrawn anterior to the inflated cuff, through the inlet to the drain lumen, into a second syringe. The collected fluid is then examined for the presence of an embryo.

The catheter is suitable for use only in the bovine and the form of the catheter makes it difficult to flush the uterus effectively, as the end of the catheter is located in one of the two horns of the uterus, and the other horn will not be efficiently flushed. As the catheter has little inherent rigidity it would likely be difficult to manipulate so as to reposition the end of the catheter in the other uterine horn. The insertion of the catheter also requires use of an outer plastic sheath and a rigid member, adding to the cost of the equipment and making sterilization more difficult. The very small diameter limits the flow of fluid for flushing, for example it would take approximately 45 minutes to supply one liter of fluid. The small diameter also limits the size of the drain lumen such that it plugs easily and will not provide a siphon effect for draining fluid from the uterus, such that some form of suction must be provided or the drain. In practice, the catheter is rarely used, even by bovine embryo transfer specialists.

Intravenous Infusion

As was mentioned above, with reference to the conventional uterine lavage method, practitioners often experience problems maintaining lavage fluid at a desired temperature. A similar problem occurs when practitioners are infusing fluid intravenously into animals. A dehydrated animal may require a fairly large infusion of fluids, typically 25-50 liters, and if the fluid is too cold, shock or hypothermia may result. This problem is particularly acute in winter when practitioners are treating animals out-of-doors or in unheated areas. Traditionally, the fluid to be infused is contained in a flexible plastic bag which is placed in a bucket of hot water for heating. To dispense the fluid, the bag is raised above the animal and the fluid descends, under the effect of gravity, through a flexible catheter into the animal. The flow rate of fluid using this method is low (typically 100 ml/min.), and it may take a significant time to dispense the contents of a bag (typically 1-5 liters). Also, significant cooling of the fluid in the bag may occur between removing the bag from the bucket and the last of the fluid being dispensed.

SUMMARY OF THE INVENTION

It is therefore an object of the present invention to provide a more convenient and efficient uterine lavage system. Further objects of the present invention include the provision of a catheter for affecting effective uterine lavages, and the provision of fluid supply apparatus for the use in uterine lavages and many other treatments.

According to a first aspect of the present invention, there is provided uterine lavage apparatus comprising a lavage fluid supply, a first catheter having a distal end for positioning in the uterus of an animal and a proximal end for communicating with the lavage fluid supply, a pair of bilateral catheters connected to the proximal end of the first catheter for extending and opening into respective horns of the uterus, and catheter locating means for locating the catheters in the uterus. The first catheter defines respective supply and drain lumens. The bilateral catheters permit fluid communication between the supply lumen and the interior of the respective horns and each define respective lumens having proximal ends in fluid communication with the supply lumen.

Preferably, the lavage fluid supply includes a pump for supplying lavage fluid. The supply may also include a lavage fluid storage tank for containing a volume of fluid, and a heater to maintain the temperature of the stored fluid within a predetermined range.

Preferably also, the lavage fluid supply may be controlled to provide a predetermined volume of lavage fluid at a predetermined flow rate.

The proximal end of the catheter may be provided with a handle including control means for remotely regulating the fluid supply means.

According to a second aspect of the present invention, there is provided uterine lavage apparatus for use in post partum animals having a gravid uterus, comprising a lavage fluid supply, a first catheter having a distal end for positioning in the uterus of an animal and a proximal end for communicating with the lavage fluid supply, a drain tube at the proximal end of the first catheter for extending and opening into the gravid uterus, and catheter locating means for locating the catheters in the uterus. The first catheter defines respective supply and drain lumens. The drain tube has a proximal end in fluid communication with the drain lumen and permits fluid communication between the interior of the gravid uterus and the drain lumen.

Preferably, the drain tube is detachable, and a number of drain tubes of decreasing length are provided to permit the apparatus to be used at successive post partum intervals with increased involution of the gravid uterus.

Preferably also, the drain tube has a distal end provided with a plurality of apertures to help prevent sealing off of the drain tube as the uterus collapses around the tube. The apertures may be provided in a sieve bulb fitted to the distal end of the drain tube.

BRIEF DESCRIPTION OF THE DRAWINGS

These and other aspects of the present invention will now be described, by way of example, with reference to the accompanying drawings, in which.

DETAILED DESCRIPTION OF THE PREFERRED EMBODIMENTS

Figure 1:
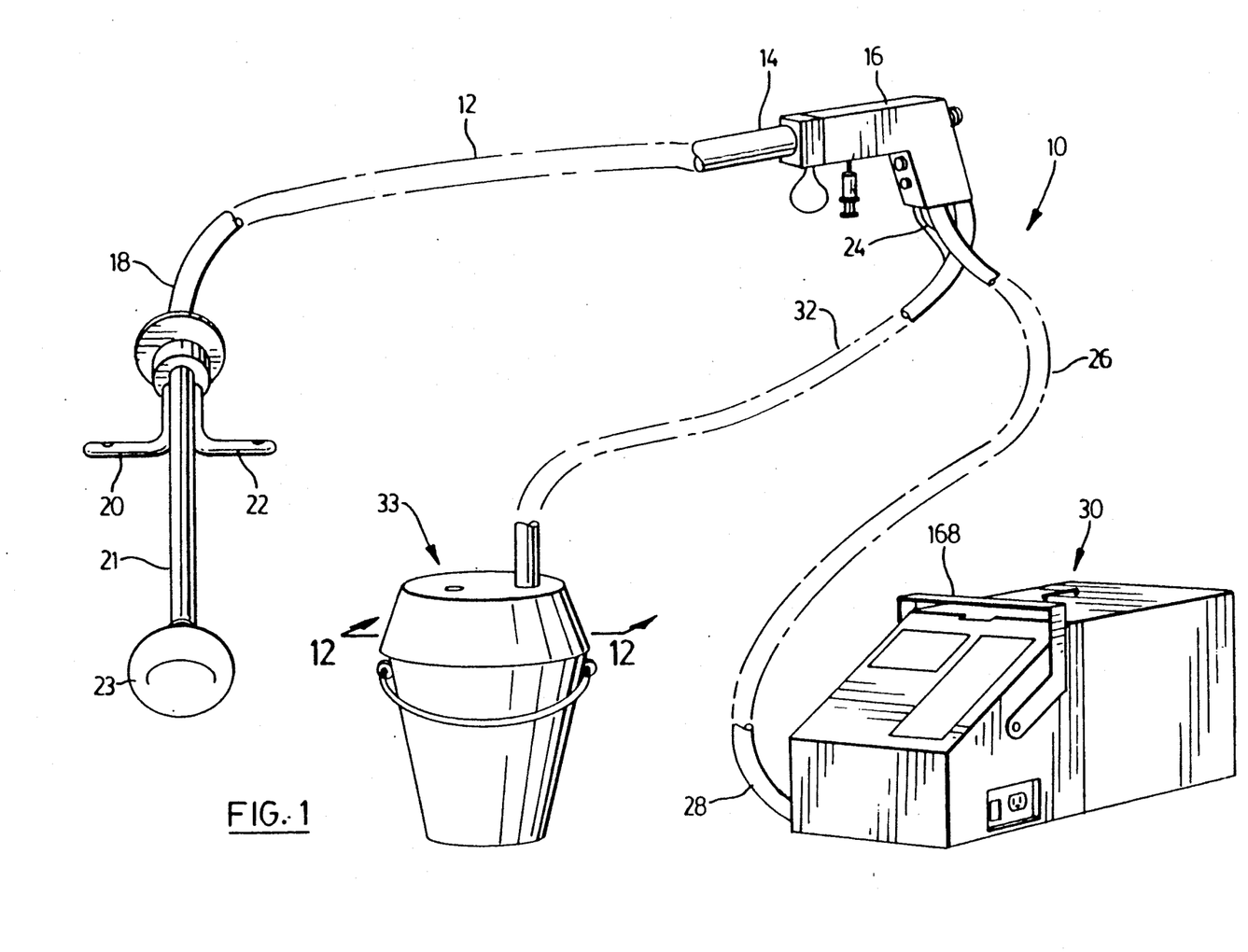
FIG. 1 is a perspective view of uterine lavage apparatus in accordance with the preferred embodiment of the present invention and including a first catheter, a pair of bilateral catheters, a drain tube, a catheter handle, and lavage fluid supply and drain apparatus.

Referring first to FIG. 1 of the drawings, uterine lavage apparatus 10 includes a first catheter 12. The proximal end 14 of the catheter 12 is attached to a catheter handle 16 and the distal end 18 of the catheter 12 is connected to a pair of smaller bilateral catheters in the form of hollow whiskers 20, 22, and a detachable first drain tube 21 fitted with a sieve bulb 23 at its distal end. The catheter handle 16 is also connected to the distal end 24 of a supply tube 26, the proximal end 28 of the supply tube 26 being in turn connected to fluid supply apparatus 30. A second drain tube 32 is also connected to the handle 16 and leads to drain apparatus 33.

In use, heated lavage fluid is pumped from the fluid supply apparatus 30 through the supply tube 26 and the handle 16 and the catheters 12, 20, 22 into the uterus of an animal. The fluid then drains from the uterus through the first drain tube 21 and the first catheter 12, the handle 16 and a second drain tube 32 connected to the handle 16. The tube 32 drains into the drain apparatus 33.

Figure 2:
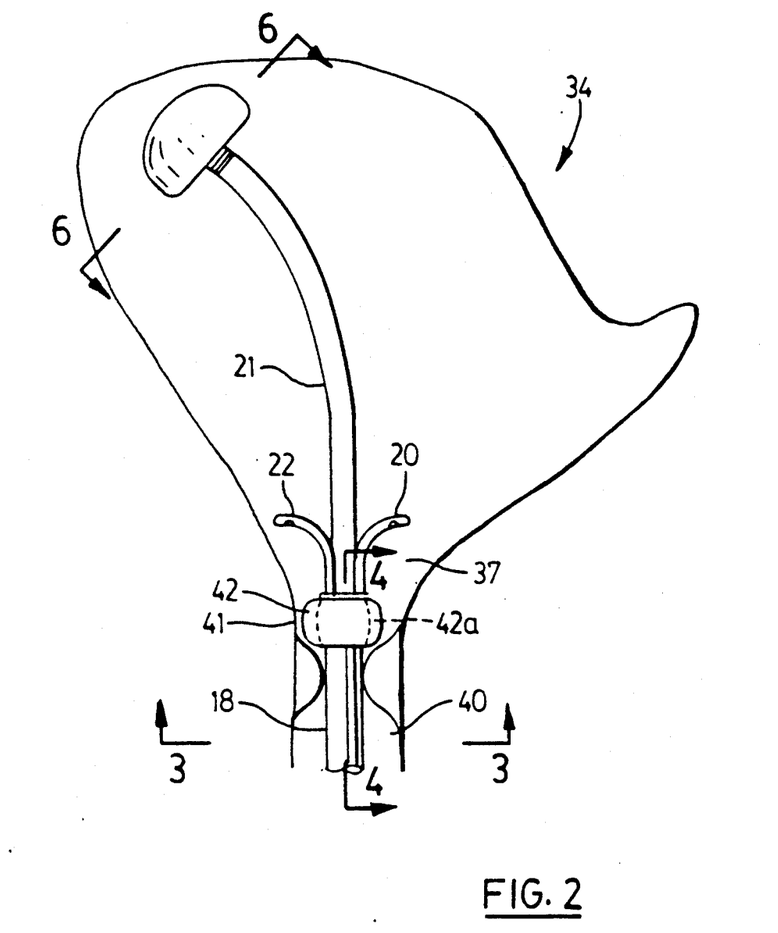
FIG. 2 is a enlarged sectional view on line 2—2 of FIG. 1 of the distal end of the first catheter, the bilateral catheters and the drain tube, shown located in the gravid uterus of a mare.

The location of the distal end 18 of the catheter 12, the whiskers 20, 22 and the drain tube 21 is illustrated in FIG. 2 of the drawings, which includes a schematic representation of the gravid uterus 34 of a post partum mare. It should be noted that the non-gravid uterus 34A is formed of two horns 36, 38, as may be seen for example in FIG. 2A of the drawings. However, pregnancy distends the uterus to an extent that the horns are no longer distinct.

Figure 3:
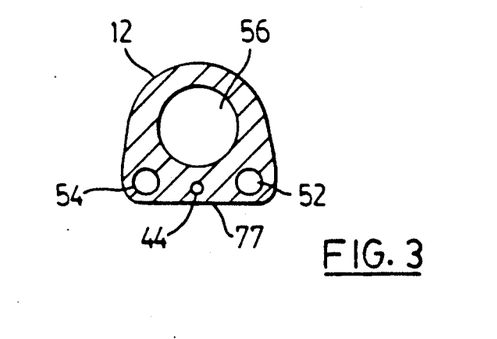
FIG. 3 is an enlarged sectional view on line 3—3 of FIG. 2.
Figure 4:
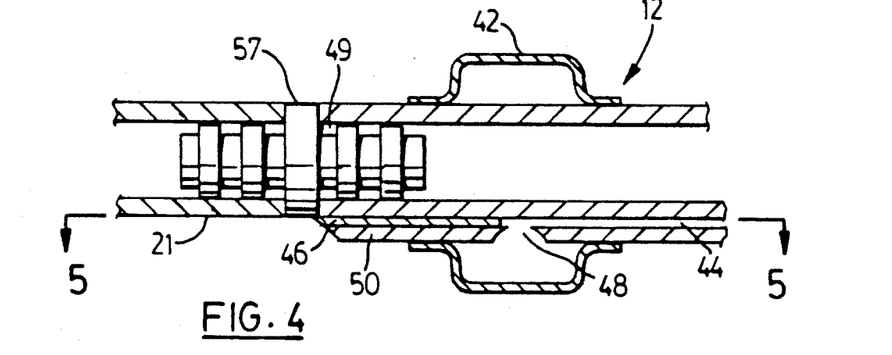
FIG. 4 is an enlarged sectional view on line 4—4 of FIG. 2.

Access to the uterus 34 is gained through the vagina 40. The veterinarian inserts the drain tube 21 and the distal end 18 of the catheter 12 through the vagina 40 and manipulates the catheter 12 such that the whiskers 20, 22 extend into the cervix, and when extended beyond the body of the uterus 37, the whiskers 20, 22 extend to the sides of the uterus and the drain tube 21 reaches well into the gravid uterus. As the catheter 12 is inserted, an inflatable cuff 42 positioned just short of the end 18 is in a deflated condition as indicated by the chain dotted lines 42A. After the catheter 12 whiskers 20, 22 and drain tube 21 have been correctly positioned the cuff 42 is inflated and expands to locate the catheter 12 in the uterus body 37 and seal the internal cervical os 41. Air is supplied to the cuff 42 through an air supply lumen 44 as seen in FIG. 3 of the drawings, which shows the cross-section of the catheter 12. If reference is made also to FIG. 4 of the drawings, it will be noted that the air supply lumen 44 is blocked short of the end of the catheter 12 by a plug 46, an opening 48 into the cuff 42 being cut through the catheter wall 50. The cuff 42 is formed of thin flexible material such as laminated silicone, approximately 0.010" thick, and thus collapses upon air being withdrawn through the lumen 44.

Figure 2A:
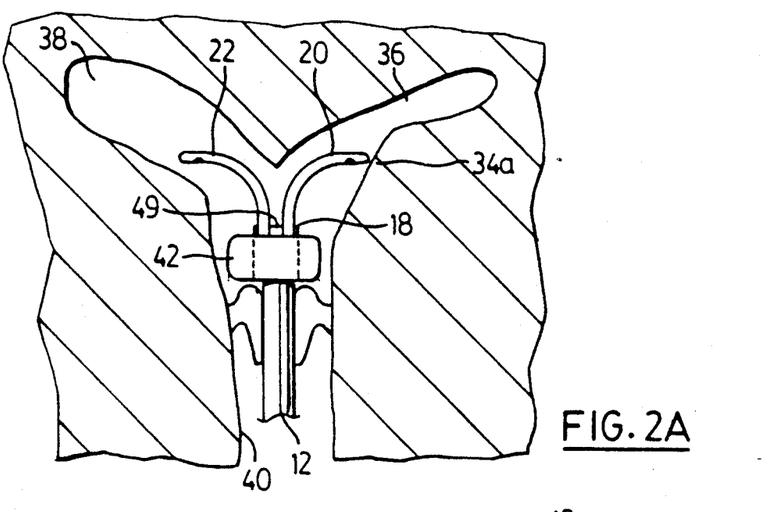
FIG. 2A is a view similar to FIG. 2, without the drain tube and showing a 10 day post partum uterus.

FIG. 2A illustrates the location of the catheter 12, and whiskers 20, 22 located in a 9-10 days post partum uterus. It will be noted that the gravid uterus has involuted from its enlarged state, as shown in FIG. 2, and thus the drain tube 21 is not required. Accordingly, fluid is withdrawn directly through the drain lumen opening 49 at the distal end 18 of the catheter 12. Also, the uterine horns 36, 38 are now much more clearly defined, and it will be noted that the whiskers 20, 22 extend into respective horns 36, 38.

Figure 5:
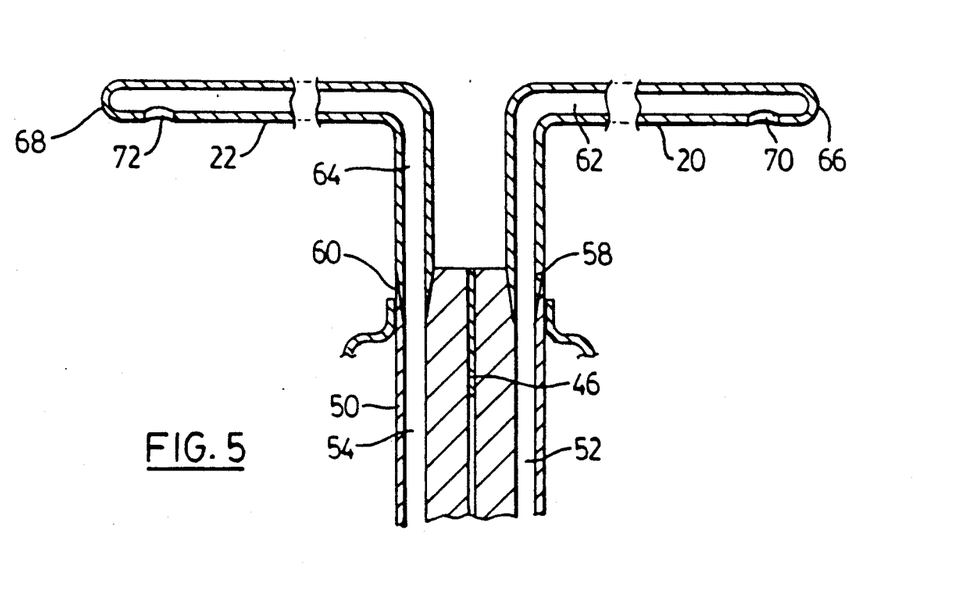
FIG. 5 is an enlarged sectional view on line 5—5 of FIG. 4.

From FIG. 3, it will be noted that the catheter 12 defines four lumens. In addition to the air supply lumen 44, there is provided two similar fluid supply lumens 52, 54 and a larger diameter drain lumen 56. If reference is now made to FIG. 5, it will be noted that the fluid supply lumens 52, 54 extend to the end of the catheter where they are widened to receive the tapered ends of the respective whiskers 20, 22 which are secured in place by means of silicone sealant. The proximal ends 58, 60 of the whiskers 20, 22 are tapered such that fluid may flow smoothly from the supply lumens 52, 54 into the lumens 62, 64 defined by the whiskers 20, 22.

After initially extending in line with the catheter 12, the whiskers 20, 22 extend bilaterally from one another such that, in use, when correctly positioned, they extend to either side of the gravid uterus 34, as shown in FIG. 2, or into the respective horns 36, 38 of the non-gravid uterus 34A, as shown in FIG. 2A. For use on mares, the angle between the whiskers 20, 22 is, conveniently, approximately 125° to match the relative orientation of the horns 36, 38. The whiskers 20, 22 have rounded distal ends 66, 68 to facilitate insertion, the respective lumen outlets 70, 72 being provided in the side walls 74, 76 just short of the respective distal ends 66, 68.

It can be seen from FIG. 3 that the catheter 12 is generally semi-circular in cross-section, the air and fluid supply lumens 44, 52, 54 being located adjacent the straight side 77 of the catheter 12. This serves to facilitate location of the catheter 12 and whiskers 20, 22 as the practitioner will be able to determine the orientation of the whiskers 20, 22 directly from the orientation of the catheter 12.

The drain lumen 56 is substantially larger than the other lumens and terminates at the distal end 18 of the catheter 12, anterior to the cuff 42. As will be seen from FIG. 4, the opening of the lumen 56 is occupied by a buttress-type coupler 57, the other end of which is located in the proximal end of the drain tube 21.

Figure 6:
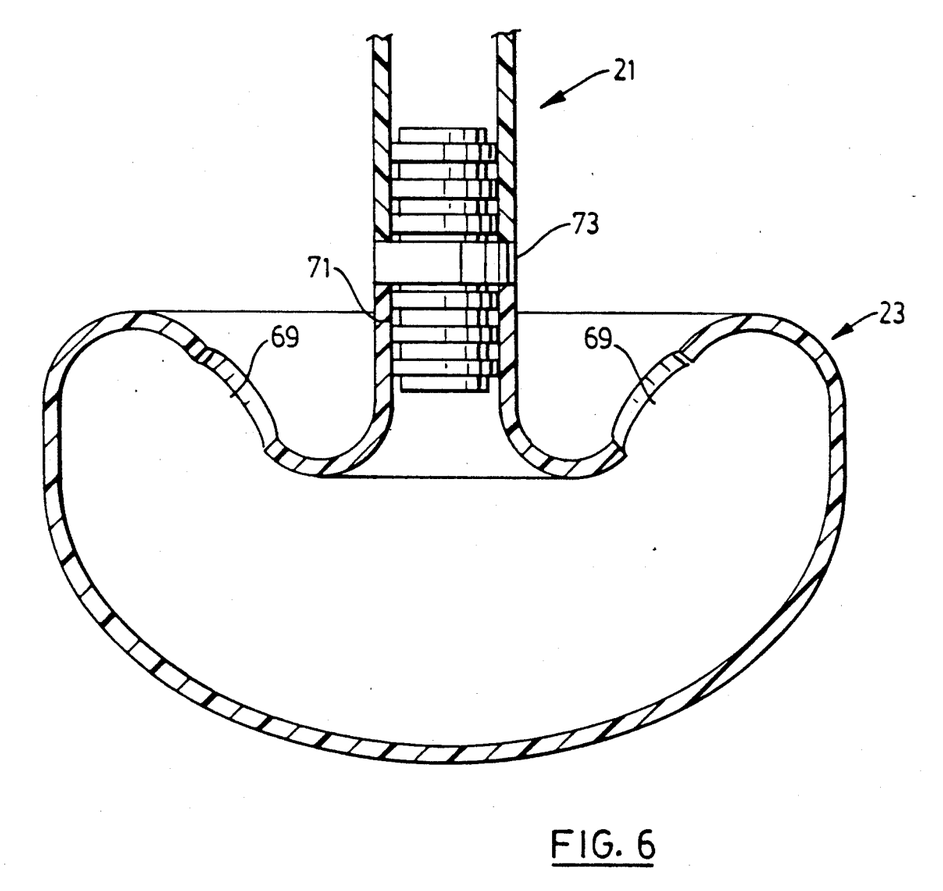
FIG. 6 is an enlarged sectional view on line 6—6 of FIG. 2.

The distal end of the tube 21 is provided with a sieve bulb 23 (FIG. 1) provided with a plurality of communicating apertures 69, as may be seen in FIG. 6 of the drawings. The bulb is formed of an originally spherical-shaped hollow ball of flexible thermoplastic material. The ball is deformed into a mushroom-like shape with a portion of maximum diameter, around 2½-3" diameter, and four or five ¼" or 3/16" diameter apertures 69 cut in the rear surfaces posterior of the area of maximum diameter. A larger ⅜" diameter aperture 71 is cut in the centre of the rear surface to receive a buttress-type coupler 73 for connecting the sieve bulb to the tube 21. The bulb 23 may be deformed for insertion into the uterus, and has sufficient memory to return to its original shape when in the uterus.

The catheter 12 and the whiskers 20, 22 are formed of unitary, autoclavable silicone extrusions, and for use with mares, the catheter 12 is between 28" and 36" long, depending on the mare, and each whisker 20, 22 between 6" and 8" long, preferably about 7" long. The drain tube 21 is also formed of a silicone extrusion and a number of drain tubes 21 of different lengths will normally be provided for use at different intervals following foaling; for example, for use after 24, 48, 72 and 120 hours, drain tubes of decreasing lengths of between 16" and 4" are provided. The same sieve bulb 23 may be utilized for each length of tube as it is easily detachable from the distal end of the tube 21. The catheter material is flexible, but is stiff enough for the catheter to be inserted without support from sheaths or rigid inserts and has sufficient memory such that the whiskers 20, 22 will always return to the original bilateral configuration. For desired rates of flow in treating mares, typically, 2-2½ liters/min., the supply lumens 52, 54 should each have a diameter of ¼", and the drain lumen a diameter of ⅝", to give a total supply lumen cross-sectional area of approximately 0.1 square inches, and a drain lumen cross-sectional area of approximately 0.3 square inches. Conveniently, the air supply lumen 44 may have a diameter of ⅛" and the cuff 42, on inflation, a length and diameter of 1" and 3", respectively.

Figure 7:
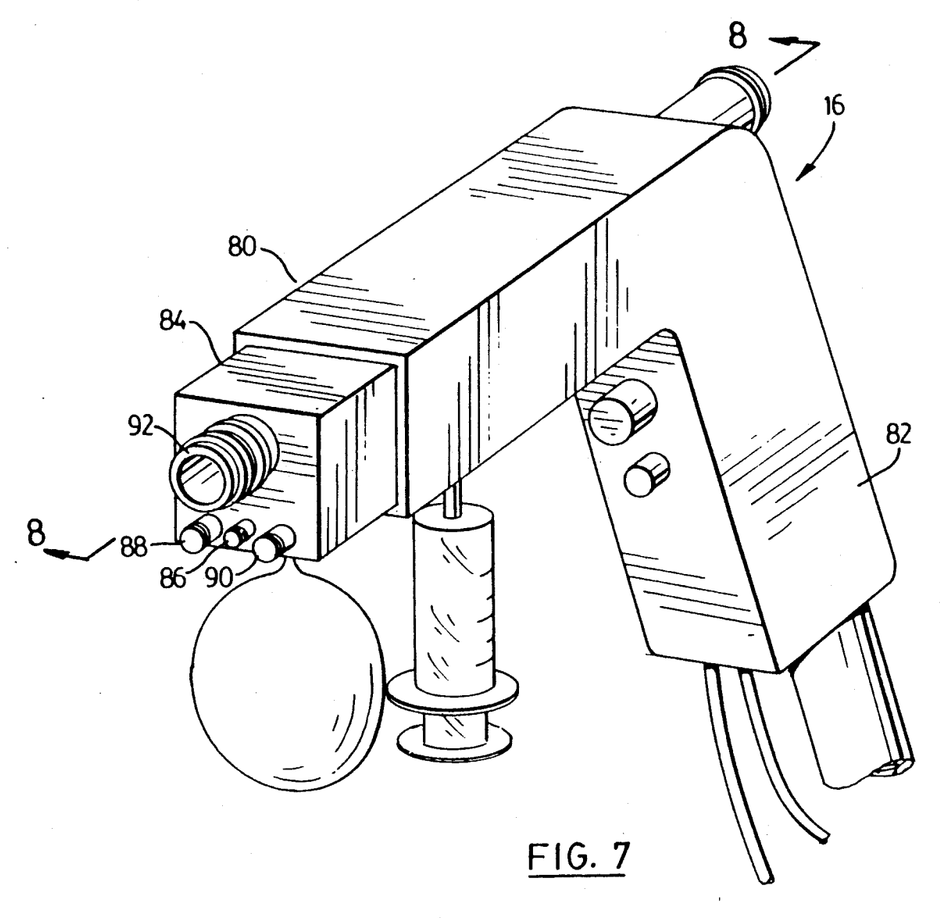
FIG. 7 is an enlarged perspective view of the catheter handle of FIG. 1.
Figures 8, 8A:
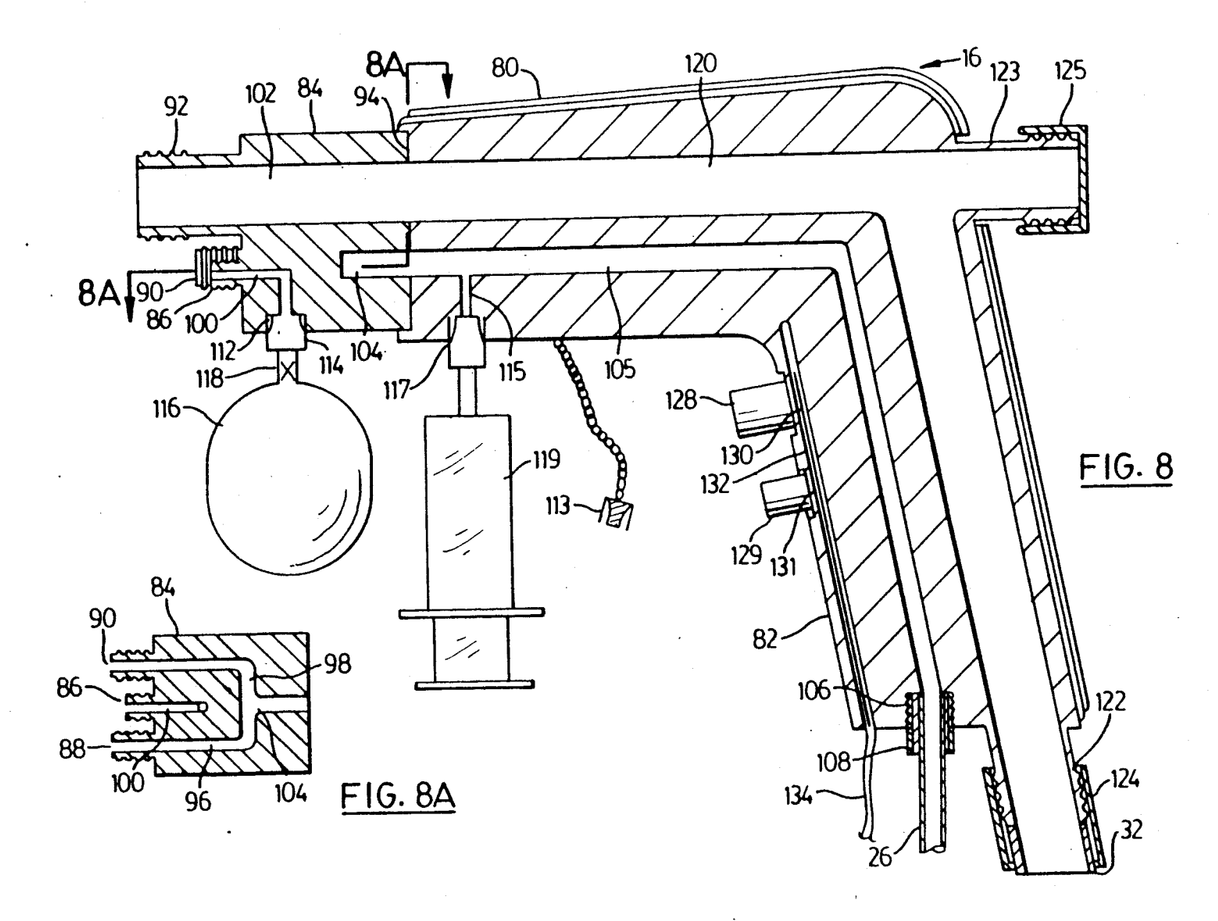
FIG. 8 is a sectional view on line 8—8 of FIG. 7.
FIG. 8A is a sectional view on line 8A—8A of FIG. 8.

The proximal end 14 of the catheter 12 is attached to the catheter handle 16, as shown in FIG. 1. The handle 16 is shown in more detail in FIGS. 7 and 8 of the drawings from which it will be noted that the handle 16 is pistol-shaped, the catheter 12 being attached to the end of the handle barrel 80 and the supply tube 32 being attached to the lower portion of the handle grip 82. The catheter 12 is actually attached to the handle 16 via an adapter 84 which is removably attached to the end of the barrel 80. If reference is made to FIG. 7, it will be noted that the adapter 84 is provided with four ribbed cylindrical fittings for engaging within respective lumens of the catheter 12. Accordingly, a small fitting 86 is sized to fit within and engage the end of the air supply lumen 44, two slighter larger fittings 88, 90 are sized and located to engage within the ends of the fluid supply lumens 52, 54 and a larger fitting 92 is sized to engage the drain lumen 56. If reference is now made to FIG. 8, it will be noted that the adapter 84 is generally cuboid in shape, and snap fits within a rectangular recess 94 provided in the end of the barrel 80. Passages 96, 98, 100, 102 (see also FIG. 8A) extend through the adapter 84 from the fittings passages 96, 98 and 102 communicating with the open passage in the handle 16. The fluid supply passages 96, 98 converge at 104 to communicate with a single fluid supply passage. The adapter air supply passage 100 passes through the adaptor to terminate in an enlarged recess 112 in the lower surface of the adapter, shaped to accomodate a complementary leur lock fitting 114 provided on an inflation bulb 116 provided with a one-way valve (shown schematically as 118). The bulb 116 is used to inflate the cuff 42 to locate the end 18 of the catheter 12 in the uterus. A suitable sphigmanometer (blood pressure) cuff bulb is supplied by White Cross Medical.

The fluid supply passage 105 in the handle 16 extends through the barrel 80 and the grip 82 to terminate in an enlarged threaded recess 106 at the lower end of the grip 82, shaped to receive a complementary fitting 108 on the distal end of the supply tube 26 from the fluid supply apparatus 30 (FIG. 1). The tube 26 is 10' long, with an internal cross-sectional diameter of ⅜", and is formed of polyamide.

The fluid supply passage 105 also communicates, via passage 115, with a port or an enlarged recess 117 provided with a leur lock fitting to engage a syringe 119 for containing post lavage medication. If such medication is not required the syringe may be removed and the passage 115 sealed with a cap 113, attached to the barrel with a fine chain.

The drain passage 120 extends through the barrel 80 and grip 82 to terminate in a ribbed fitting 122 which extends from the lower part of the grip 82. The fitting 122 is shaped to engage a snap collar 124 provided on the end of the drain tube 32. A port provided with a further fitting 123 is located at the top rear of the grip 82 for accessing the passage 120, for use, for example in hysteoscopic examination using a fibreoptic scope. In the illustrated example in FIG. 8, the fitting 123 is closed by a cap 125.

The grip 82 of the handle 16 includes two triggers 128, 129 of the normally open-momentary on type which operate respective switches 130, 131 provided in a channel 132 defined by the grip 82. The triggers 128, 129 are waterproof so as to protect and insulate the switches 130, 131 and also the wires 134 which lead from the switches 130, 131 to the fluid supply apparatus 30 and the drain apparatus 33 (FIG. 1).

Figure 9:
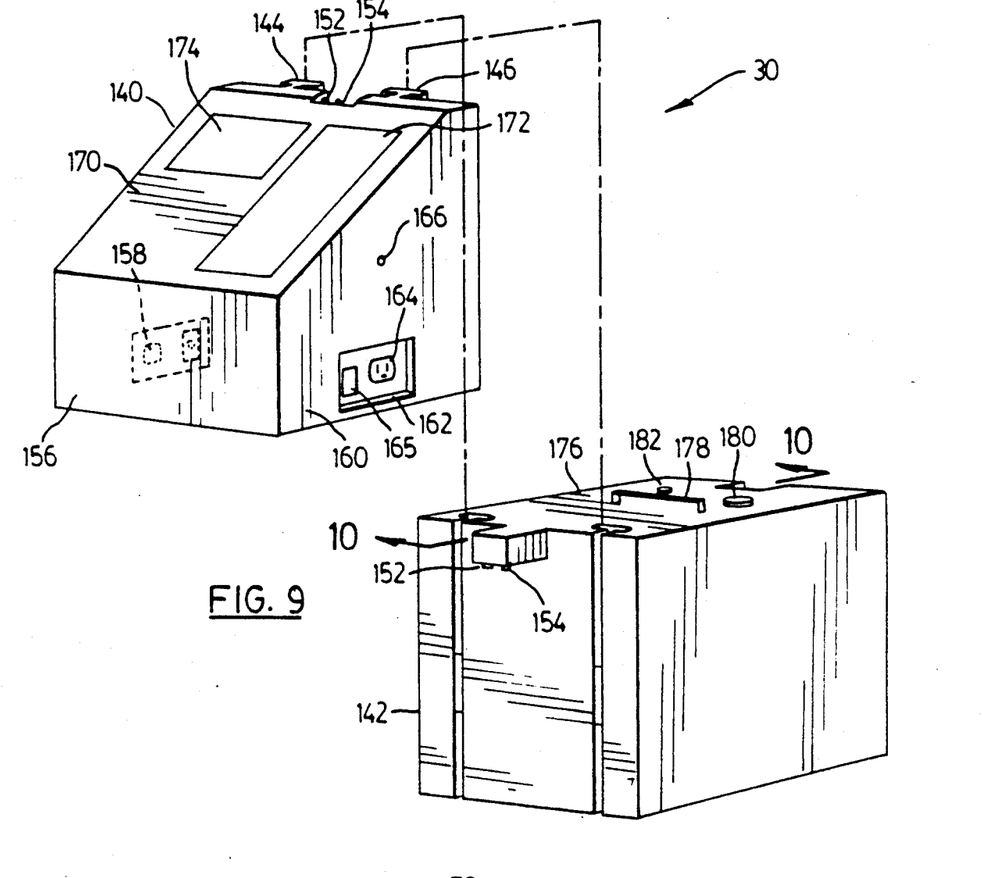
FIG. 9 is an enlarged perspective view of the lavage fluid supply apparatus of FIG. 1, shown with the two components of the supply apparatus separated.
Figure 10:
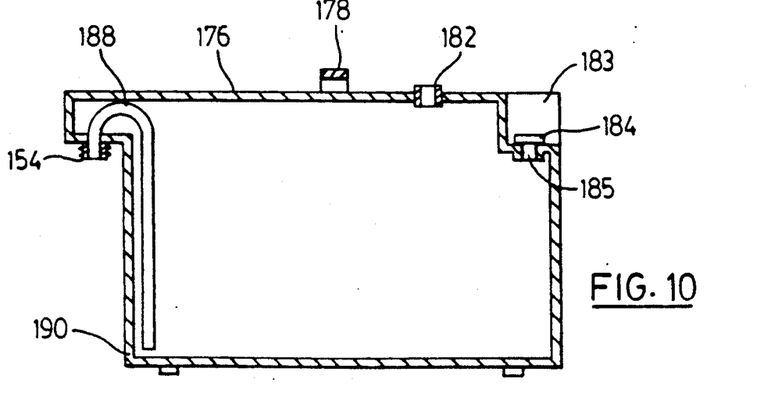
FIG. 10 is a sectional view on line 10—10 of FIG. 9.
Figure 12:
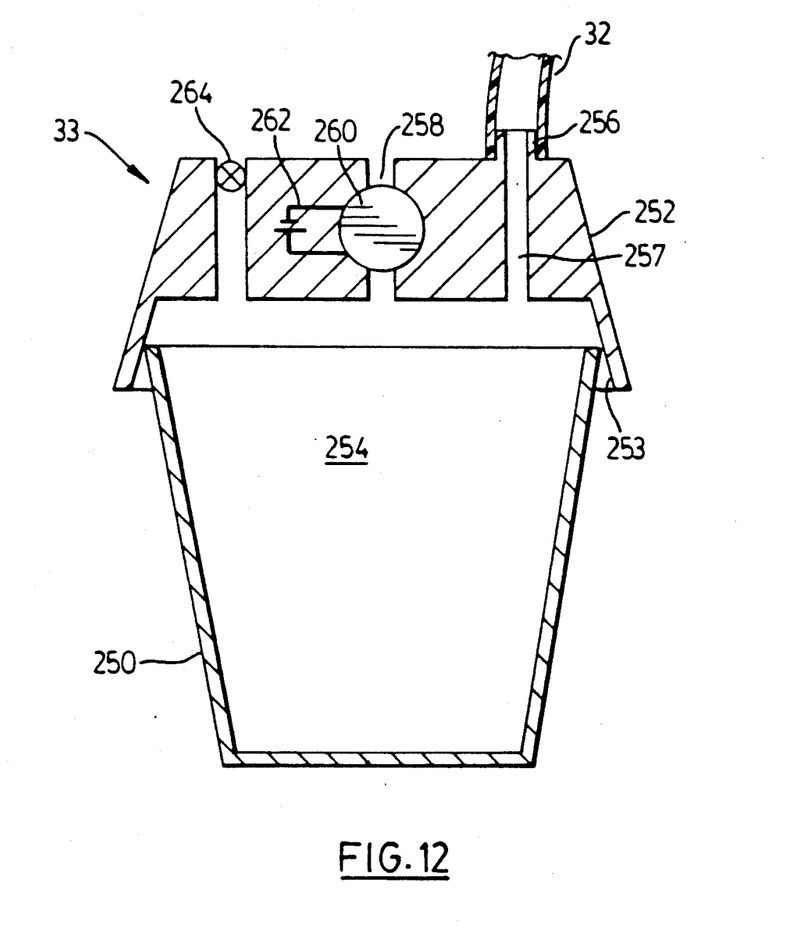
FIG. 12 is a schematic sectional view on line 12—12 of FIG. 1 showing the drain apparatus.

The provision of the pistol-like handle 16 facilitates handling of the catheter 12 and the provision of the triggers 128, 129 allows a practitioner to remotely control the fluid supply apparatus 30 which is shown in more detail in FIGS. 9 and 10 of the drawings and the fluid drain apparatus which is shown in more detail in FIG. 12 of the drawings.

Conveniently, the handle 16 and adaptor 84 are formed of high temperature polycarbonate, such as that sold under the Lexan trade mark.

It will be noted from FIG. 9 that the fluid supply apparatus 30 comprises two separable parts, a pump unit 140 and a fluid tank 142. The pump unit 140 and tank 142 engage by means of T-shaped projections 144, 146 provided on the unit 140 and complementary T-shaped slots 148, 150 provided on the front wall of the tank 142. Two male, $\frac{3}{8}$" long polytetraflouroethylene (such as sold under the Teflon trade mark) couplings 152, 154 are provided on a projection from the tank 142 to be received by corresponding openings in a recess at the rear of the unit such that fluid may be drawn from the tank through coupling 154 and returned to the tank 142 through coupling 152.

The fluid pump unit 140 is generally rectangular when viewed from above, one side wall 156 of the unit 140 being provided with a fluid supply outlet 158 and the other side wall 160 provided with a rectangular recess 162 containing a mains plug fitting 164 for engaging a mains supply (not shown) and a fuse holder 165. The side wall 160 also includes a circular recess 166 to receive a projection on the end of the carrying handle 168 (shown in FIG. 1). The upper face 170 of the unit is sloped and includes a membrane type key pad 172, a suitable pad being supplied by Memtron, and a 6"×6" LCD display screen 174. The key pad 172 is waterproof and allows a practitioner to program the unit as will be described below.

The tank 142 is generally cuboid in form and is provided, on its upper wall 176, with a carrying handle 178. Also provided on the top wall 176 are a removable filler cap 180 and a hydrophobic filter 182, conveniently a 0.2u Millex PFG$_{50}$. As fluid is drawn from the tank 142 by the pump unit 140, the filter 182 allows air to pass into the tank to replace the volume of fluid being removed. In this example, the volume of the tank, which is conveniently formed of high temperature polycarbonate such as Lexan, is 15 liters. To increase the volume of fluid available, an additional tank may be added in tandem to the tank 142 and is connected thereto by means of a fluid coupling similar to that provided between the pump unit and the tank. It will be noted that the tank is provided with a rectangular recess 183 in its rear wall having female fittings 184 for this purpose. Suitable quick connect $\frac{3}{8}$" P.V.C. fittings are available from Festo. When an additional tank is being used, the filter 182 will be closed such that fluid is drawn from the additional tank, and of course the plugs 185 will be removed.

As the fluid couplings 152, 154 between the pump unit 140 and the tank 142 are located at the upper end of the tank, it is necessary to provide a communicating passage between the supply coupling 154 and the lower part of the tank, and this is achieved by providing flexible tubing 188, suitably $\frac{3}{8}$" diameter Teflon tubing, which extends from the top wall 176 almost to the floor 190 of the tank.

In order to heat the fluid in the tank, an electrical heating element is provided as part of a heat cartridge in the pump unit 140. A temperature sensor is provided in the cartridge to monitor the temperature of fluid coming from the tank and, in conjunction with the unit 140, the sensor controls the operation of the element, as will be described later.

Figure 11:
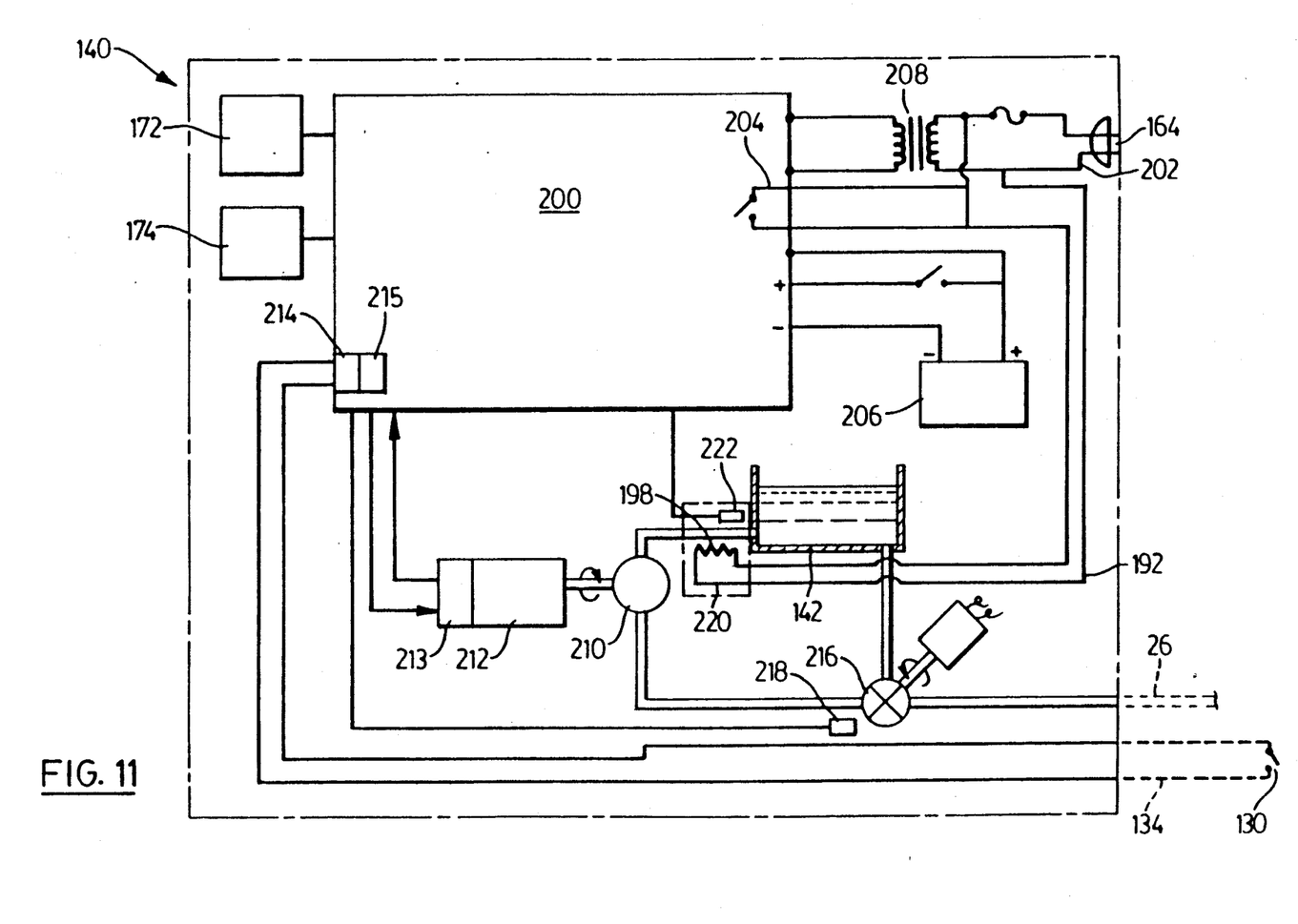
FIG. 11 is a schematic representation of the control system of the fluid supply of FIG. 1.

The heating element 198 and the pump unit 140 are operated by means of a micro-processor control unit 200, such as the MBM 27C64-25 available from Electrosonic Ltd. and FIG. 11 of the drawings illustrates, in schematic form, the control system of the unit 140. The micro-processor 200 may be supplied preprogramed, a practitioner using the key pad 172 to access one of the available programs. Alternatively, the unit may be programmed for a particular purpose by the practitioner.

The heating element 198 is powered from normal mains supply through a line voltage input 202, which is directly available to the element 198 through a heater relay 204. The pump unit (excluding the heating element 198) is powered by a rechargable battery 206.

The unit 140 includes a dialysis-type pump 210 driven by a motor 212 provided with an on board integral tachometer 213. A suitable stainless steel pump is available from Tuthill under model no. B9046M, driven by a Pottman 9434F 886 12 V.d.c. motor fitted with a Hewlett Packard HEDS 5310 tachometer. Power for the motor 212 is controlled by means of an actuator switch 214, which is itself controlled by the switch 130 provided on the catheter handle 16. For safety of animal and operator a field effect sensor 215 is provided such that activator switch 214 can only be operated by the switch 130 when the main supply is disconnected. However, where large volumes of fluid are being supplied over a longer time period, the operator may overide this safety feature in order to power the heater and maintain the temperature of the fluid.

In the simplest operating mode, the practitioner uses the screen 174 and keypad 172 to select a fluid flow rate and the total volume of fluid to be supplied and, after locating the catheter 12 in the animal, activates the unit by means of the trigger 128 and switch 130. The motor 212 operates at the speed necessary to obtain the desired fluid flow and fluid is pumped until the desired volume of fluid has passed through the pump 210. The measurement of the volume of fluid supplied is achieved by use of the tachometer which records the number of cycles the pump makes and thus, as the volume of fluid pumped by one cycle is known, the total volume of fluid can be determined. The tachometer conveniently comprises an encoder and a counter and also serves to control the speed of operation of the motor 212, to allow better control of pump operation. However, for lower flow rates, it is difficult to accurately measure the relatively slow speed of rotation of the motor by means of an encoder. Accordingly, a motor driven divider valve 216, such as Putman #3435F 348 is provided downstream of the pump 210 and may be set to divert a predetermined proportion of the flow from the pump 210 back to the tank 142. Thus, for a small flow rate, the motor and pump may be operated at relatively high speeds and a divider valve 216 used to divert a relatively large proportion of flow back to the tank. A position sensor 218 in the form of an on board encoder, is fitted on the valve 216 to measure the setting of the valve 216 by measuring the direction and number of turns of the valve to give an exact percentage value of function, and by comparison of the valve setting with the motor speed, the micro-processor 200 can determine the flow rate of fluid actually reaching the catheter 12.

The heat cartridge is illustrated at 220 between the tank 142 and the pump 210, and includes the heating element 198 and a sensor 222 which measures the temperature of the fluid as it leaves the tank. If the temperature of the fluid is below a predetermined level, the heating element 198 is activated, as are the pump and divider valve motors. To recirculate the heated fluid back to the tank, the valve 216 is set such that all of the flow is returned to the tank. In this example, the heat cartridge 220 includes a 1250 W, ¾" diameter×7" length firerod heater as sold by Watlow Inc. and a lithiumdiode thermistor to act as a sensor.

Reference is now made to FIG. 12 of the drawings which illustrates, in somewhat schematic form, the drain apparatus 33 located on a typical semi-plyable pail 250. The apparatus is self contained and includes a housing 252 provided with a frustoconical inner surface 253 for engaging the top lip of the pail to form an enclosed chamber 254. A coupling 256 is provided on the upper face of the housing for mating with the proximal end of the second drain tube 32. A passage 257 extends from the coupling 256 directly into the chamber 254. A further passage 258 is provided between the chamber 254 and the exterior of the housing via a vacuum pump 260. The pump 260 is powered by a 12 V d.c. battery 262 provided in the housing and is capable of providing 20" Hg vacuum. The pump 260 is controlled by the trigger 129 on the handle 16 (FIG. 8) and is normally activated by the operator during a lavage when the normal siphon action is not draining sufficient lavage fluid from the gravid uterus. A floating poppet valve 264 is provided in the housing to allow exhaust of air from the pail 250 under normal siphon drainage, and is set to close an activation of the pump 260, which produces a vacuum in the chamber.

While the apparatus is not in use, the pump unit 140 is connected to the mains electrical supply to recharge the battery 206 and power the tank heater 192. The apparatus is portable, having a total dryweight of 32 lbs., the control unit measuring 9" wide by 12" high by 10" long, and the tank measuring 9" wide by 12" high by 12" long, and thus the unit may be disconnected from the mains supply, with a filled tank, and taken directly to the farm or stable where the animal to be treated is located. The detachable tank 142 allow the practitioner to carry a substantial volume of sterilized and heated fluid to the work site and thus save a considerable amount of time which would otherwise be lost in heating and preparing the fluid on site.

On reaching the site, the practitioner uses the keypad 172 and screen 174 to select the desired program, specifying a desired volume flow rate, total volume to be supplied and desired fluid temperature, as described above with reference to the operation of the unit 140. The catheter 12 is then inserted into the animal and the whiskers 20, 22 and drain tube 21 located in the uterus 34. The configuration of the catheter 12 gives the practitioner a clear indication of the correct alignment of the catheter as it is inserted and thus provides for easier positioning of the whiskers 20, 22. When the catheter 12 is in the desired position, the practitioner operates the bulb 116 to inflate the cuff 42 and thus locate and seal the catheter 12 in place. The practitioner then grips the catheter handle 16 and depresses the trigger 128 to activate the pump 210. The pump continues to operate until the desired volume of fluid has been pumped. However, if the practitioner wishes, the trigger 128 may be released to deactivate the pump 210.

During the lavage operation, fluid is being pumped through the supply tube 26, catheter handle 16, catheter 12 and whiskers 20, 22 into the uterus. The pressurised fluid tends to dilate the uterus to facilitate effective flushing. Conveniently, the port pressure of the fluid is between 0 and 10 p.s.i. After volume of fluid, typically 1.5-2 liters, has been pumped into the uterus, the fluid begins to drain from the uterus, due to siphon effect and contraction or involution of the uterus, through the first drain tube 21, the drain lumen 56, the catheter handle 16 and the drain tube 32 into the pail 250. In some cases, particularly when a gravid uterus is being lavaged, the siphon effect will not be readily induced, and in such circumstances the operator will activate the vacuum pump 260 to ensure that the fluid is drained from the uterus.

The main application of the apparatus is in the preparation of post partum mares for breeding The first flush is carried out around twenty four hours after foaling using 6 liters of hot saline (1% sodium chloride and 110° to 120° F.) input at a rate of 2 liters/min., the heat tending to accelerate the contraction or involution of the uterus from its enlarged state following foaling, the contraction also serving to help drain the fluid from the uterus, as mentioned above. The initial flushing is followed by at least two subsequent flushes, 24 hours apart, until the drain fluid is clear from start to finish of the lavage operation. The mare is then left for four to five days and a culture taken and the uterus visually checked via hysteoscopic means. If the culture proves to be clear, the mare is bred when she comes into heat approximately nine days after foaling and preliminary testing of the apparatus indicates that a conception rate of upwards 85% is achieved when the apparatus and method described are used.

Figure 13:
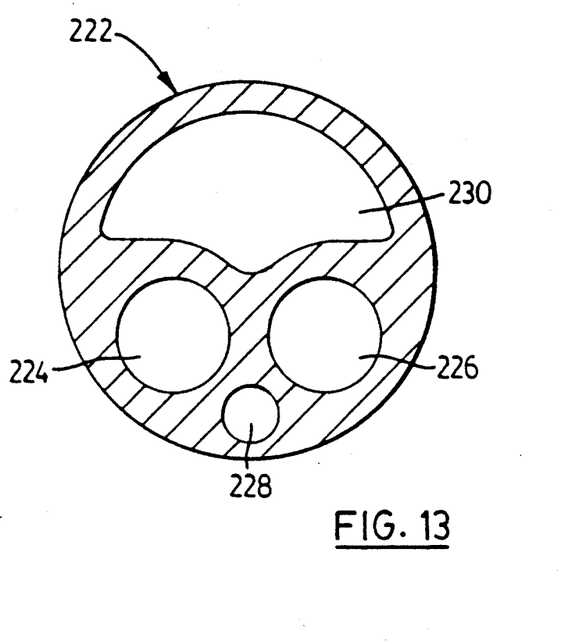
FIG. 13 is a sectional view of an alternative first catheter for use in a further embodiment of the present invention.
Figure 14:
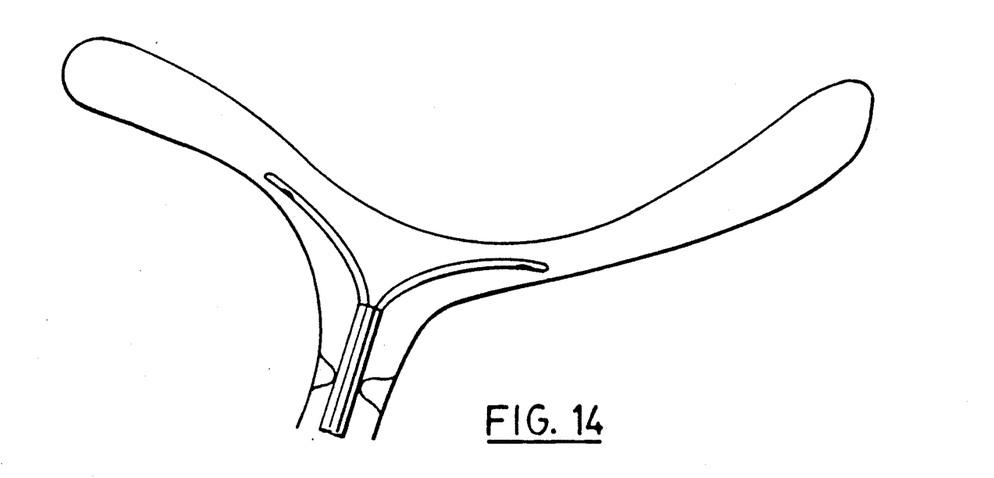
FIG. 14 is a view from above the first catheter of FIG. 13 and corresponding bilateral catheters shown located in the uterus of a 30+ day post partum mare.

In addition to treating post partum mares, a modified apparatus may be used for treating mares for other purposes. As the channel to the uterus, and the uterus itself, contracts following foaling, it is desirable to use a smaller catheter, and a suitable catheter is illustrated in FIG. 13 of the drawings, and also in FIG. 14, where the catheter is shown provided with corresponding bilateral catheters and located in the uterus of a mare (at least 30 days post partum). The catheter 222 is ⅛" diameter and defines four lumens, two fluid supply lumens 224, 226, an air supply lumen 228 and a drain lumen 230. The fluid and air supply lumens are circular in cross-section and have diameters of 3/16" and 1/16", respectively. The drain lumen 230 is of generally semi-circular cross-section, the straight edge of the lumen being provided with a central recess of 1/16" radius. The bilateral catheters, or whiskers 232, 234 are slightly longer than the post partum whiskers 20, 22 and are 8-10" in length, have a diameter of 3/16" and taper slightly from the lumens 224, 226 to the free ends. To provide greater rigidity to ease handling and insertion the whiskers are formed of polytetraflouroethane, such as Teflon (Trade Mark). Clearly, the other apparatus of the system must be adapted to suit the smaller catheter, for example, the handle 16 must be provided with a different adaptor to accomodate the different shaped and configured catheter 222.

Apart from dimensions, the catheter 222 is similar to the post partum catheter 12. Fitted with this catheter 222, the apparatus may be used to treat mares suffering from chronic endometritis (infection of the uterus). Such infection may cause mares to lose foals and may also inhibit production of hormones necessary for successful pregnancy. The conventional treatment of chronic endometritis is to scrape or curette the uterine walls to stimulate blood flow to the wall surface to increase the availability of white blood cells, specifically neutrophils, for fighting the infection. It has been found that flushing the uterus with hot water also brings blood to the surface of the uterus, and also cleans the uterus. The lavage operation is generally easier to perform than curetting the uterus walls and does not result in a large amount of debris being left in the uterus, as occurs with curetting. For such a flushing operation it has been found that providing a total volume of 3 liter of lavage fluid delivered at an intermittant 1.5 liters/min. and a temperature of 100°-120° F. is preferable.

After a mare has been bred by natural service, as for example thoroughbreds traditionally are, the apparatus, fitted with catheter 222, may be used to lavage the residue which remains in the uterus after service, as this residue may lie in the uterus and cause infection. The operation involves little danger of damaging the embryo, as the embryo will not descend from the ovary to the uterus until approximately five days after service.

The apparatus may also be used in determining why certain mares do not have successful pregnancies. By placing a filter in the drain tube, a practitioner can lavage a fertilized egg from the uterus for analysis, and this will often indicate why the mare is not conceiving or carrying the pregnancy up to day 35. A total lavage fluid volume of 1.5-2.0 liters delivered at a flow rate of 1 liter/min. and a temperature of 100° F. would normally be sufficient for this purpose.

The pump unit and tank may also be used separately of the uterine catheters for administration of fluid intravenously. The pump unit allows fluid to be heated before being administered and the use of the pump allows the fluid to be dispensed at approximately five times the rate available with gravity feeding from fluid bags. This allows the practitioner to carry out the operation more quickly, and as the fluid is heated before infusion the body temperature of the animal will remain constant, reducing considerably the risk of shock or hypothermia. Depending on the degree of dehydration and heartrate, isotonic fluids such as Lactated Ringers by Baxter, can be given at a temperature of 100° F. and flow rates between 250-300 ml/min to deliver a total volume of 25-50 liters (for an adult horse or cow).

The apparatus may also be used for use in bronchial alveolar lavages (BAL) where a lung is flushed and the drain fluid tested to determine what cells are present in the lung. Typically, fluid supply rates are around 500-1000 ml/min. at a temperature of 100° F. until approximately 100 ml of fluid has drained from the lung, usually after 750 ml has been infused.

The apparatus may also be used for supplying fluid for use in surgical lavages as it provides an easily controllable flow of sterile fluid. Further, the apparatus has utility for use in arthroscopic lavage (AL) and, when provided with a specific oesophaged catheter, in providing differential intrapleural pressure (DIP).

Thus it may be seen that the apparatus described provides for convenient and efficient uterine lavages, which would appear to increase conception rates considerably. The fluid supply apparatus also has application for providing a convenient source of heated sterile fluid.

It will be clear to those skilled in the art that the particular apparatus described above is merely exemplary, and that various modifications and improvements may be made to the invention without departing from the scope of the invention.

We claim:

1. Uterine lavage apparatus comprising:
   lavage fluid supply means for supplying fluid at above ambient pressure;
   a first catheter defining a supply lumen and a drain lumen and having a distal end for positioning in the uterus of an animal and a proximal end, the supply lumen in communication with the fluid supply means and extending from said proximal end to said distal end, and the drain lumen extending from said distal end to said proximal end;
   a pair of bilateral catheters extending from said distal end of the first catheter for positioning in respective horns of the uterus, each of said pair defining respective lumens for fluid communication between said supply lumen and the interior of the respective horns; and
   means on the first catheter for sealing the catheters in the uterus.

2. Uterine lavage apparatus, as claimed in claim 1, in which the lavage fluid supply means includes pump means.

3. Uterine lavage apparatus, as claimed in claim 2, in which the pump means is controllable to supply fluid at different flow rates.

4. Uterine lavage apparatus as claimed in claim 3, and further comprising lavage fluid drain means in fluid communication with the drain lumen for drawing lavage fluid from the uterus through the drain lumen.

5. Uterine lavage apparatus, as claimed in claim 2, in which the lavage fluid supply means includes fluid storage means.

6. Uterine lavage apparatus, as claimed in claim 5, in which the fluid storage means is in the form of a tank.

7. Uterine lavage apparatus, as claimed in claim 6, in which the tank is detachable from the pump means and is provided with detachable couplings for fluid communication between the pump means and the tank.

8. Uterine lavage apparatus, as claimed in claim 5, in which the fluid supply means includes fluid heating means.

9. Uterine lavage apparatus for use in lavaging a gravid uterus comprising:
  lavage fluid supply means for supplying fluid at above ambient pressure;
  a first catheter defining a supply lumen and a drain lumen and having a distal end for positioning in the uterus of an animal and a proximal end, the supply lumen in communication with the fluid supply means and extending from said proximal end to said distal end, and the drain lumen extending from said distal end to said proximal end;
  a drain tube for extending into the gravid uterus having a proximal end in communication with said drain lumen and a distal end for location in the gravid uterus to permit fluid communication between the interior of the gravid uterus and the drain lumen; and
  means on the first catheter for sealing the catheter in the uterus.

10. Uterine lavage apparatus, as claimed in claim 9, in which the lavage fluid supply means includes pump means for supplying lavage fluid at above ambient pressure.

11. Uterine lavage apparatus, as claimed in claim 10, in which the pump means is controllable to supply fluid at different flow rates.

12. Uterine lavage apparatus, as claimed in claim 11, in which the pump means is in the form of a variable speed pump.

13. Uterine lavage apparatus, as claimed in claim 11, in which the lavage fluid supply means includes valve means, downstream of the pump means and controllable to restrict the supply fluid flow rate.

14. Uterine lavage apparatus, as claimed in claim 13, in which the valve means is in the form of a divider valve which may be set to supply and recirculate respective portions of fluid from the pump means to the first catheter and back to the pump means.

15. Uterine lavage apparatus, as claimed in claim 13, in which the pump means is in the form of a motor driven pump, and the valve means is in the form of a motor driven divider valve.

16. Uterine lavage apparatus, as claimed in claim 13, and further comprising control means for controlling the pump means and the valve means to provide a fluid supply at a predetermined flow-rate.

17. Uterine lavage apparatus, as claimed in claim 16, in which the control means further controls the pump means to provide a predetermined total volume of fluid.

18. Uterine lavage apparatus, as claimed in claim 17, in which the control means includes a tachometer for monitoring the cycle rate of the pump means and producing a signal proportional to the said cycle rate, the control means deactivating the pump means after a predetermined number of cycles when a predetermined volume of fluid has been supplied.

19. Uterine lavage apparatus, as claimed in claim 18, and further a valve position sensor, for producing a valve position signal, the control means compares the tachometer signal with the valve position sensor to determine the total volume of fluid supplied.

20. Uterine lavage apparatus, as claimed in claim 19, in which the control means includes a microprocessor programmed to include different programmes for controlling the setting of the pump means and valve means to provide a selected flow rates of fluid.

21. Uterine lavage apparatus, as claimed in claim 20, in which the control means includes a keypad and display means mounted on the exterior of the pump unit whereby an operator may set the control means via the keypad.

22. Uterine lavage apparatus as claimed in claim 10, and further comprising fluid drain apparatus connected to the first catheter and in communication with the said drain lumen for drawing lavage fluid from the uterus of the animal.

23. Uterine lavage apparatus as claimed in claim 22, which the drain apparatus includes a vacuum pump for drawing lavage fluid from the uterus.

24. Uterine lavage apparatus as claimed in claim 23, in which the drain apparatus includes a chamber for receiving lavage fluid from the uterus, the chamber provided with a valve to permit air to be displaced from the chamber by lavage fluid, activation of the vacuum pump causing said valve to close and creating a vacuum in said chamber.

25. Uterine lavage apparatus as claimed in claim 22, in which the lavage fluid supply means includes fluid storage means.

26. Uterine lavage apparatus as claimed in claim 25, in which the fluid storage means is in the form of a tank.

27. Uterine lavage apparatus as claimed in claim 26, in which the tank is detachable from the pump means and is provided with detachable couplings for fluid communication between the pump means and the tank.

28. Uterine lavage apparatus as claimed in claim 27, in which two fluid couplings are provided, one fluid coupling for withdrawal of fluid from the tank, and the other fluid coupling for return of fluid to the tank.

29. Uterine lavage apparatus as claimed in claim 28, in which the tank is provided with the rear wall including fluid couplings for engaging corresponding fluid couplings on the front wall of a further tank to thus increase the volume of fluid available from the apparatus.

30. Uterine lavage apparatus as claimed in claim 25, in which one of the tank and the pump means is provided with T-shaped projections for engaging corresponding T-shaped slots provided in the other of the tank and the pump means.

31. Uterine lavage apparatus as claimed in claim 30, in which the pump means is provided with a rear wall and the tank is provided with front wall, with detachable fluid couplings being provided in the front wall of the tank for engaging corresponding fluid couplings on the rear wall of the pump means.

32. Uterine lavage apparatus as claimed in claim 25, in which the fluid supply means includes fluid heating means.

33. Uterine lavage apparatus as claimed in claim 32, in which monitoring means are provided for monitoring the temperature of fluid drawn from the fluid storage means and activating the pump means to circulate fluid through the heating means when the fluid temperature falls below a first predetermined level.

34. Uterine lavage apparatus as claimed in claim 26, in which the tank means is provided with a filter in communication with the interior and exterior of the tank to permit air to be drawn into the tank to replace fluid being withdrawn from the tank.

35. Uterine lavage apparatus as claimed in claim 23, in which handle means are provided at the proximal end of the first catheter.

36. Uterine lavage apparatus as claimed in claim 35, in which the handle means includes switch means for activating and deactivating the lavage fluid supply means.

37. Uterine lavage apparatus as claimed in claim 36, in which the handle means includes switch means for activating the fluid drain apparatus.

38. Uterine lavage apparatus as claimed in claim 37, in which the handle means includes:
a fluid supply passage in fluid communication with the supply lumen and having a distal end connected to the first catheter and a proximal end for connection to a supply catheter extending from the lavage fluid supply means; and
a drain passage in fluid communication with the drain lumen and having a distal end connected to the first catheter and a proximal end for connection to a drain tube.

39. Uterine lavage apparatus for use in supplying and draining lavage fluid to and from the uterus of an animal comprising:
a first catheter defining a supply lumen and a drain lumen and having a distal end for positioning in the uterus and a proximal end, the supply lumen extending from said proximal end to said distal end and the drain lumen extending from said distal end to said proximal end;
a pair of bilateral catheters extending from said distal end of the first catheter for positioning in respective horns of the uterus, each said bilateral catheter defining a lumen for fluid communication between said supply lumen and the interior of the respective horns; and
means on the first catheter for sealing the catheter in the uterus.

40. Uterine lavage apparatus, as claimed in claim 39, in which the catheters are of flexible material and may be deformed from an original configuration to assist insertion in the uterus, the material having sufficient memory to return to said original configuration when unrestrained.

41. Uterine lavage apparatus, as claimed in claim 40, in which two supply lumens are provided in the first catheter, each said supply lumen in fluid communication with a respective lumen of the bilateral catheters.

42. Uterine lavage apparatus, as claimed in claim 41, in which the first catheter has a substantially planar surface portion extending along a substantial portion of the length of the catheter, the bilateral catheters lying in a plane generally parallel to the substantially planar surface portion to facilitate correct alignment of said bilateral catheters in the uterus.

43. Uterine lavage apparatus, as claimed in claim 42, in which the first catheter is of substantially semi-circular cross-section.

44. Uterine lavage apparatus, as claimed in claim 43, in which the bilateral catheters have respective proximal and free distal ends, the proximal ends connected to the distal end of the first catheter, and the free distal ends being rounded, openings being provided short of the distal ends for fluid communication between the lumens and the interior of the uterine horns.

45. Uterine lavage apparatus, as claimed in claim 44, in which the first catheter is between 28" and 36" in length, and each of the bilateral catheters is between 8" and 9" in length.

46. Uterine lavage apparatus, as claimed in claim 42, in which handle means are provided at the proximal end of the first catheter.

47. Uterine lavage apparatus as claimed in claim 46, in which the handle means includes:
a fluid supply passage in fluid communication with the supply lumen and having a distal end connected to the first catheter and a proximal end for connection to a supply catheter extending from lavage fluid supply means; and
a drain passage in fluid communication with the drain lumen and having a distal end connected to the first catheter and a proximal end for connection to a drain tube.

48. Uterine lavage apparatus, as claimed in claim 47, in which the locating means is in the form of an inflatable cuff positioned around the distal end of the first catheter, the cuff in fluid communication with an air supply lumen provided in the first catheter.

49. Uterine lavage apparatus for use in supplying and draining lavage fluid from a gravid uterus comprising:
a first catheter defining a supply lumen and a drain lumen and having a distal end for positioning in the uterus of an animal and a proximal end, the supply lumen in communication with the fluid supply means and extending from said proximal end to said distal end, and the drain lumen extending from said distal end to said proximal end, a drain tube for extending into the gravid uterus having a proximal end in communication with said drain lumen and a distal end for location in the gravid uterus to permit fluid communication between the interior of the gravid uterus and the drain lumen; and
means on the first catheter for sealing the catheter in the uterus.

50. Uterine lavage apparatus as claimed in claim 49, and further comprising a seive bulb at the distal end of the drain tube, said seive bulb having a portion of maximum diameter and a plurality of drain apertures posterior of said portion at an area of lesser diameter whereby collapse of the uterus around the seive bulb does not block the apertures.

51. Uterine lavage apparatus as claimed in claim 50, in which the seive bulb is mushroom shaped.

52. Uterine lavage apparatus as claimed in claim 51, in which the seive bulb is of a resilient material which may be deformed for insertion into the uterus but has sufficient memory to return to the undeformed condition when unrestrained.

53. Uterine lavage apparatus as claimed in claim 52, and further comprising a pair of bilateral catheters extending from said distal end of the first catheter, each said bilateral catheter deforming a lumen for fluid communication between said supply lumen and the interior of the uterus.

54. Uterine lavage apparatus as claimed in claim 53, in which the catheters are of flexible material and may be deformed from an original configuration to assist insertion in the uterus, the material having sufficient memory to return to said original configuration when unrestrained.

55. Uterine lavage apparatus, as claimed in claim 54, in which two supply lumens are provided in the first catheter, each said supply lumen in fluid communication with a respective lumen of the bilateral catheters.

56. Uterine lavage apparatus, as claimed in claim 55, in which the first catheter has a substantially planar surface portion extending along a substantial portion of the length of the catheter, the bilateral catheters lying in a plane generally parallel to the substantially planar surface portion to facilitate correct alignment of said bilateral catheters in the uterus.

57. Uterine lavage apparatus, as claimed in claim 56, in which the first catheter is of substantially semi-circular cross-section.

58. Uterine lavage apparatus, as claimed in claim 57, in which the drain lumen is of at least equal cross-sectional area to the combined cross-sectional area of the supply lumens.

59. Uterine lavage apparatus, as claimed in claim 49, in which the total cross-sectional area of the supply lumen is at least 0.1 square inches.

60. Uterine lavage apparatus as claimed in claim 50, in which the drain lumen is detachable from the first catheter.

61. Uterine lavage apparatus as claimed in claim 60, in which a number of drain tubes of progressively shorter lengths are provided, each for use at different intervals as the uterus progressively contracts after the animal has given birth.

62. Uterine lavage apparatus as claimed in claim 61, in which drain tubes are between 16" and 4" in length.

63. Uterine lavage apparatus, as claimed in claim 50, in which handle means are provided at the proximal end of the first catheter.

64. Uterine lavage apparatus as claimed in claim 63, in which the handle means includes:

a fluid supply passage in fluid communication with the supply lumen and having a distal end connected to the first catheter and a proximal end for connection to a supply catheter extending from lavage fluid supply means; and a drain passage in fluid communication with the drain lumen and having a distal end connected to the first catheter and a proximal end for connection to a drain tube.

65. Uterine lavage apparatus as claimed in claim 64, in which the locating means is in the form of an inflatable cuff positioned around the distal end of the first catheter, the cuff in fluid communication with an air supply lumen provided in the first catheter.

66. Uterine lavage apparatus, as claimed in claim 65, in which the handle means further includes an air passage having a distal end in fluid communication with the air supply lumen and a proximal end in fluid communication with air supply means.

67. Uterine lavage apparatus, as claimed in claim 66 in which the air supply means is in the form of a hand-operated bulb pump provided with a one-way valve and a pressure relief valve.

68. Uterine lavage apparatus as claimed in claim 64, in which the handle means includes a sealable port for the fluid supply passage, said port including means for connecting and infusion device for infusing drugs into the lavage fluid supply.

69. Uterine lavage apparatus as claimed in claim 64, in which the handle means includes a sealable port for the drain passage for receiving a scope for visual examination of the uterus.

70. Uterine lavage apparatus as claimed in claim 56, in which the first catheter is between 28" and 36" in length, and each bilateral catheters is between 6" and 8" in length.

* * * * *